United States Patent [19]

Cochran

[11] Patent Number: 5,488,438
[45] Date of Patent: Jan. 30, 1996

[54] VISION CONTROL GLASSES

[76] Inventor: William A. Cochran, 17905 W. 209th St., Spring Hill, Kans. 66083

[21] Appl. No.: 321,444

[22] Filed: Oct. 11, 1994

[51] Int. Cl.$^6$ ........................................ G02C 7/16
[52] U.S. Cl. ................... 351/45; 351/41; 351/46; 473/59
[58] Field of Search ................ 351/41, 44, 45, 351/46, 47, 63, 111, 124, 131, 132; 273/183.1, 190 A; 473/59

[56] References Cited

U.S. PATENT DOCUMENTS 3,308,478  8/1965  Tate ............................ 473/59
4,168,111  9/1979  Baines ......................... 351/46
4,969,649  11/1990  Lugiewicz ................... 273/190 A Primary Examiner—William L. Sikes
Assistant Examiner—Huy Mai

[57] ABSTRACT

Improvements in eye glasses for training in bowling, bowling per se, and bowling competition; eye glasses of a surround-type covering the front and sides of the entire field of vision of both human eyes; selective masking of the eye glasses whereby to form two substantially vertical, substantially parallel windows through which the bowler can see the lane in front of him/her and the pins that he/she is aiming for, but has the view in both lateral directions, at least two bowling lane widths, masked from his/her vision.

6 Claims, 1 Drawing Sheet

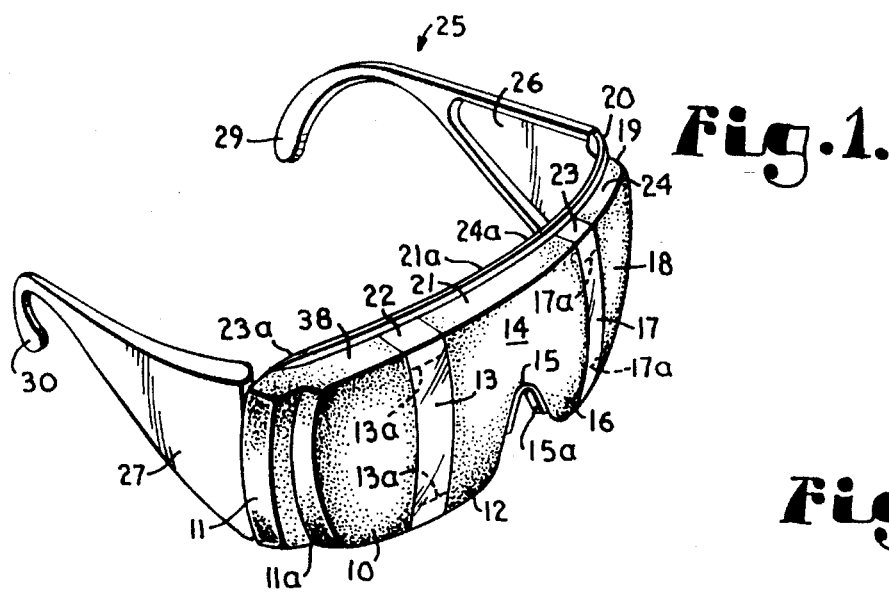
Fig.1.
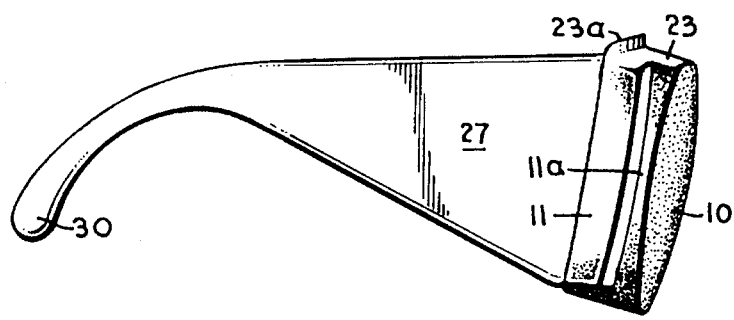
Fig.2.
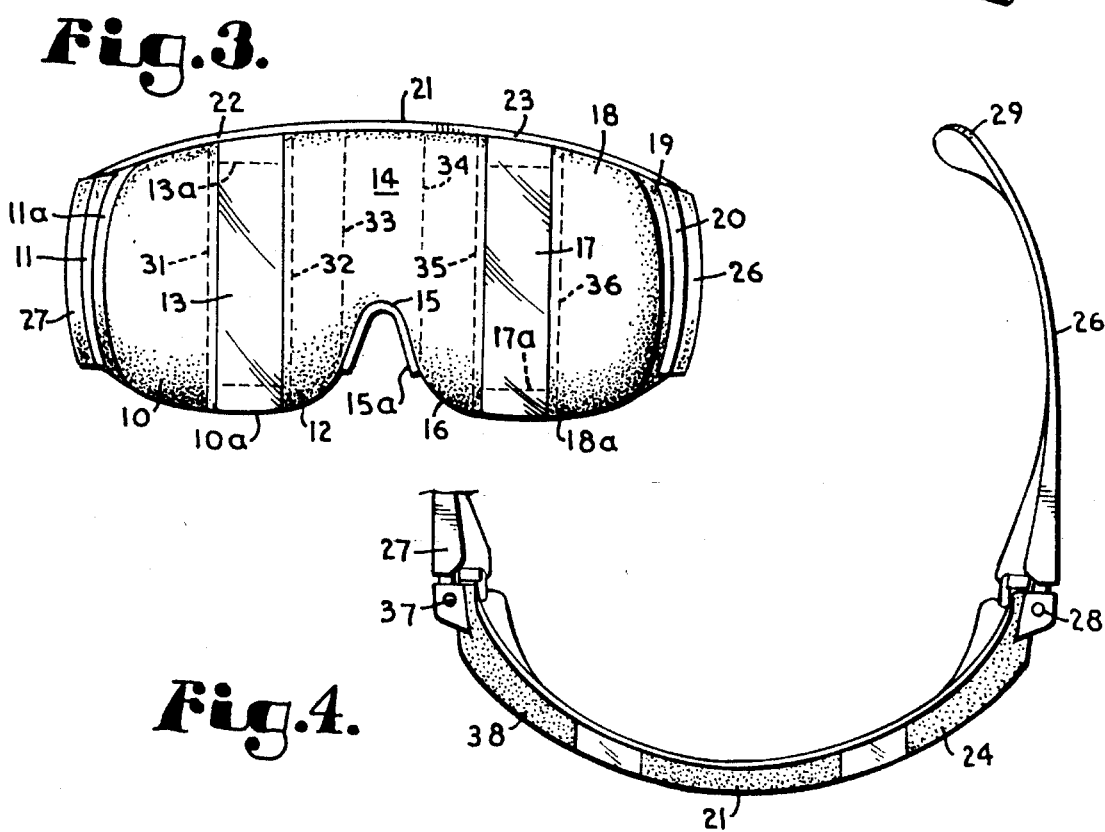
Fig.3.
Fig.4.

VISION CONTROL GLASSES

BACKGROUND OF THE INVENTION

Certain bowling terms will be first described so that the subject invention and the remarks thereon will be completely clear and understandable. Thus, a bowler picks up his/her ball and positions him/herself on the approach area, which is about four feet wide and sixteen feet long. A foul line is at the end of the approach area and the bowler cannot touch across the foul line during the delivery. Delivery is accomplished when a bowler releases his ball across the foul line.

The area across the foul line is referred to as the lane and that area that a bowler tries to get the ball to roll on in about the first five to sixteen feet is called the target area of the lane. A bowling game consists of ten frames, each with a maximum score of 30. A series consists of three or four games during a normal "League" session. The greater the degree of accuracy achieved in placing the ball and releasing such with a consistent speed, the greater the score, if the bowler has chosen the correct target, line and speed to use.

Some of the more common ways that the bowling delivery can be degraded by distraction or lack of concentration are:

(1) Rushing the approach—That is, walking too fast for the speed of the arm swing, which action causes the ball to arrive at the foul line late in the delivery and usually will mean that the bowler delivers the ball to the left of the target line intended.

(2) Taking one's eyes off the target—to be successful in hitting his/her intended target line with the ball, the bowler's eyes must remain concentrated on the target during the delivery.

(3) Off-balance at the foul line—an off-balance approach and delivery can cause bowlers to so vary their footwork and delivery as to attempt to compensate for the out of balance condition which will effect the path of the ball and the consistency of the delivery.

BRIEF DESCRIPTION OF THE INVENTION

The subject device comprises a bowling aid operative to eliminate distractions or distraction of the bowler in question caused by other bowlers entering the bowler's field of peripheral vision. By restricting, limiting and narrowing the subject bowler's vision to a narrow field essentially in front of him, the subject device allows the subject bowler to concentrate more on his target area or the line along which he/she wants to roll the ball. This, per se, will improve both bowling accuracy and consistency in the sport. After a bowler has become proficient in those physical skills required to obtain bowling success, he/she becomes more dependent on a positive mental state of mind. This reinforces the pattern and action built up into skill by repetitive practice and competition. However, the slightest distraction can shift or disorder this positive, grooved state of mind and cause the bowler to make or effect a bad or insufficient delivery. This effects the particular frame being bowled and such poor performance can carry forward to effect subsequent frames and, perhaps, the entire series.

As is well known, the method of scoring in bowling is such that consecutive strikes count more than strikes that are separated. A distraction causing a bad count or frame in the middle of a string of strikes can cost a bowler as much as sixty pins. An average game for men who regularly bowl is a score of about one-hundred and sixty. Distraction is a substantial cause of the lowness of this score compared to the ideal three-hundred. Distraction can keep any player from achieving his/her maximum potential. For the higher average bowler—at or above a 200 average —distraction can cause a 10–30 pin lower average.

Common bowling courtesy dictates what is called an "one-lane courtesy." That is, a particular bowler lets the bowler on an adjacent lane finish the delivery of their ball before they step up to position for their own delivery. More and more, in recent years, especially among the higher average bowlers, there has come and appeared the adoption of the "two-lane courtesy." That is, a given bowler waits for the bowlers two lanes on each side of him to complete their delivery. As can be well imagined, this causes bowling for the entire league to take longer than if only one-lane courtesy were used. The bowling proprietor has the problem that leagues that follow are caused to start late, or he/she may have to alter the starting time of the earlier leagues to allow for this slower bowling. Either or both of these solutions will cost him/her money, because he gets less usage of his equipment per hour of operation.

With use of the subject eye device(s) by all bowlers that desire the two lane courtesy, the problem is, per se, eliminated. Such using bowlers will not see anything that other bowlers are doing in their peripheral vision and thus, there is no need to wait completion of action in the extra lane and normal league play can continue. (Even when a bowler allows for the one or two lane courtesy without the visual devices in question, they find, from time to time, that when they are in their delivery process, some bowler two or three lanes away will approach the foul line at about the same time. This can be most distracting, and in most cases, cannot be anticipated.) Such surely causes some break in the bowler's concentration that negatively effects the accuracy and consistency of his/her delivery just at the point where there is no time to make a correction or discontinue the delivery.

Use of the subject visual control devices will eliminate this problem, as well, because such restrict vision in the peripheral areas where the other bowlers are performing their deliveries. Yet further, while wearing the subject devices, it is the fact that any off-balance condition in the approach to the foul line is magnified. This fact further causes the bowler to develop a better approach as a result of wearing the devices. In other words, such a bowler will be trained to have better balance naturally during the bowling delivery, just by wearing the subject device. A better balanced approach automatically leads to a more consistent delivery and better scores.

Yet another area of distraction that not uncommonly occurs exists when another bowler may tell the subject bowler to go ahead with his/her delivery, but will locate him/herself or stand on the approach or part way up on the approach. This can cause the subject bowler to rash his approach and delivery of the ball, often causing another sub-par delivery and performance. Again, the subject devices help solve this problem by keeping the bowler's vision restricted to his/her own target area and away from such other possible distractions.

Because of the peripheral vision limiting attributes of the subject devices, they, in effect, narrow a bowler's field of view. Such narrowing forces the bowler to concentrate more on his target and gives him/her a feeling of being essentially alone and effectively unable to be distracted by the action of other bowlers around him/her. External visual distractions are, for the most part, thus completely eliminated. Such facts improve the bowler's concentration into the target area where it is most needed, allowing the bowler to make the most accurate delivery possible to him/her.

The situation encountered in average leagues is a mixture of bowlers that desire a two-lane courtesy with ones that only require one lane courtesy. Even a bowler that only requires a one lane courtesy can be affected by a bowler requiring a two-lane courtesy if the bowler using such two-lane courtesy shows displeasure at the bowler using one lane courtesy for the break in concentration. If bowlers that require the two-lane courtesy all wear the subject device, then all of the bowlers can perform essentially continuously without interfering with each other. League play can finish more quickly and everyone's performance will be improved.

THE PRIOR ART

Applicant is aware of the following references relating in various manner and to a greater or lesser degree to limitation of vision for various purposes:

Douglass, R. S., U.S. Pat. No. 2,663,021, "Optical Device For Golf Instruction," issued Dec. 22, 1953;

Baines, U.S. Pat. No. 4,168,111, issued Sep. 18, 1979 for "Golfing Glasses;"

Jampolski, U.S. Pat. No. 3,628,854, issued Dec. 21, 1971 for "Flexible . . . Lens;"

Taupin, U.S. Pat. No. 4,106,119, issued Aug. 15, 1978 for "Eye Shades;"

Gilson, U.S. Pat. No. 4,698,022, issued Oct. 6, 1987 for "Visual Occlusion Apparatus . . . ;"and Peters et al, U.S. Pat. No. 5,177,510, issued Jan. 5, 1993 for "Alignment Glasses."

OBJECTS OF THE INVENTION

A number of the objects and purposes of the invention have been heretofore set forth and discussed in the Application sections "Background Of The Invention" and "Brief Description Of The Invention."

The present invention is generally concerned with providing a bowling aid in the nature of a pair of glasses which screen the entire forward, lateral, vertical and down views of the eyes save for limited pathways in front of each eye, whereby to eliminate lateral and peripheral distracting motions and appearances being able to reach the eye of the bowler as he/she begins and carries out his/her delivery.

In the subject bowling aid eye control devices, the provision solely of a limited, limitable point of view for each eye pupil of the bowler is achieved in such manner that full privacy of the visual perception of the bowler is obtained.

The provision of such a device which achieves bowler visual privacy actually enables the running of the competition of a given league in the minimum time, yet with maximum good results individually for the bowlers and collectively for the leagues and further benefits the proprietor of the bowling establishment.

A further object of the invention is to provide visual devices that tend to eliminate the erroneous bowling action of rushing the approach, that is, walking too fast for the speed of the arm swing.

Still another object of the invention is to minimize the bowler's tendency to take his/her eyes off the target at any time during the delivery so the bowler's eyes are always concentrated on the target during the delivery.

Yet further, an object of the invention is to provide visual devices for use in bowling which minimize or eliminate the chances of the bowler being off-balance at the foul line, thus avoiding the necessity of the bowlers' varying their footwork in delivery so as to attempt to compensate for an out of balance condition.

Another object of the invention comprises the provision of a visual bowling aid operative to eliminate visual distractions of the bowler in question caused by other simultaneously operating bowlers entering the bowler's field of peripheral vision as he/she does bowl.

Another object of the invention is to restrict, limit and narrow the subject bowler's vision to a narrow field in front of him, whereby the subject bowler is able to concentrate solely on his/her target area or the line along which he/she wants to roll the ball.

Another object of the invention is to produce a device which, when used over a period of time, in the proper manner, will improve both bowling accuracy and consistency in the sport.

Other and further objects of the invention have appeared and will appear in the course of the following description thereof.

DRAWINGS

In the drawings, which form a part of the instant invention such are to be read in conjunction therewith, embodiments of the invention are shown and, in the various views, like numerals are employed to indicate like parts.

FIG. 1 is a three-quarter perspective view from the front and above of a specific embodiment of the invention, utilizing solid or material lenses to cover the entirety of both eyes.

FIG. 2 is a side view of the device of FIG. 1 taken from the left in fig one looking to the right.

FIG. 3 is a front view of the, device of FIGS. 1 and 2.

FIG. 4 is a top view of the device of the preceding three Figures with a portion of the right-hand ear in the view (overlying or engaging ann) removed under FIG. 3 so as not to interfere with that view.

EYE VISION LIMITS

It should be noted that partial approaches to the subject problem or attempts at partial solutions of the problems involved with applicant's device have been seen in the Art. There are many purposes for which vision may usefully be restricted, particularly in training situations for flying and athletics. With respect to flying, applicant has an advertising sheet showing a "Francis IFR Hood" characterized as "This is the original IFR hood and it is by far the most effective for restricting vision to the instruments." There is also provided an instrument training visor, IFR training glasses (U.S. Pat. No. 4,698,022), the Jeppesen Sanderson Deluxe IFR Hood and a device called a "Super Hood." Gilson, U.S. Pat. No. 4,698,022, shows a somewhat occluding device with transparent lower central parts of the eye pieces to limit the -view of the user to the airplane instruments. The patents to Baines, U.S. Pat. No. 4,168,111, issued Sep. 18, 1979 for "Golfing Glasses," show ordinary glass frames where a central slit is provided to purportedly concentrate the look of the golfer downwardly toward the ball. Peters et al, U.S. Pat. No. 5, 177,510 shows individual glasses of ordinary character like that of Baines, see FIG. 1, where bands of visibility may be provided at opposite angles (typically horizontal or vertical for various training purposes), particularly for golfing, runners, basketball throwers, even bowlers. None of these devices, in any way, can satisfactorily accomplish the task and important purposes of the applicant's device.

STRUCTURE AND FUNCTION

A basic concept of the subject invention is that substantially the entire visual field of the bowler, golfer or other sportsman who may be using this device for whatever purpose, save for a specifically limited part for each eye, is opaqued across the entire front of the field of vision and rearwardly of the eye socket to the head, per se, where the ear engagements lie next to the head. It is important to understand that these glasses or eye protectors must have this basic structure of enclosing the entire visual area exist except for the fact that they are not limited in strictly controlled areas of visual access of the eyes within the applied glasses to the outer environment. The general enclosing shape of the device around the eyes is not generally new save in the key opaquing thereof.

GENERAL DESCRIPTION OF THE INVENTION

The improvement comprises eyeglasses for aiding bowling play by limiting peripheral vision of the bowler during play and practice. It should be understood that some bowlers must also wear primary sight-corrective glasses during bowling. In this case, the training glasses must be of sufficient contained volume within the front lens, the side edges thereof and the side panels with their engagements to receive, preferably without contact, the corrective glasses. Otherwise, the glasses do not need to be of such free internal space, as will be described.

The device typically comprises an elongate single front panel or pair of front panels joined together centrally in a central panel, which normally, when the glasses are being worn by the user, substantially overlie and surround both eyes of the user. This remark includes the eye cavities, sockets or brow recesses of the users. That is, the periphery of the socket zone is enclosed for each eye and the central bridge of the nose also enclosed, preferably, while the side edges of the eye socket are enclosed or opaqued.

It should be noted that each eye has "peripheral" vision to the left and to the right, as well as upwardly and downwardly, in its socket. We are concerned with either eye seeing distracting motion, particularly to the left and right of the socket, including across the bridge of the nose ,and ahead (on the sides) of the bowler.

Front panels of the device of the Figures include a right eye front panel 10, right eye right end pieces 11 and 11*a*, a right eye inner noseward section 12 and a non-opaqued clear portion 13. There is a nose overlying panel 14, which preferably has sponge robber 15*a* or sponge plastic resilient member lined recess 15 thereon.

With respect to the left eye socket zone, there is the noseward side panel 16, the transparent slit or opening 17 and the leftmost panel portion 18. The side edges are seen at 19 and 20.

It should be noted that the actual eyeglass construction, per se, as shown in these views, save for the opaquing of portions of the view panels, is not novel. A top center edge portion 21 carries view panels 22 and 23, which may be either opaque or clear. However, portion 21 is preferably entirely opaque. The right hand top edge 38, which also overlies the side edge portions 11, is preferably opaqued, as is the same side top edge 24.

The front panel construction for both eyes of FIGS. 1–4, inclusive, shows essentially an eyeglass construction with interior depth therein (see FIGS. 1 and 4) whereby other glasses may be worn therewithin. Even assuming conventional eyeglasses in use, a closer contact, that is, less arcuate and rearward depth of the front lens panels may be employed if contact between the training and corrective glasses is not objectionable to the user.

Eyeglasses, particularly those involving motion and exertion of the user and wearer, typically require side arms or panels with ear overlying pieces. In this construction, the left hand side panel as seen at 25 with an opaqued front portion 26, with a pivot pin connection to one of the, side edges 11 or 19 or 20 with the pivot pins seen at 37 and 28 in FIG. 4. The ear engaging tabs are seen at 29 and 30.

It should be noted that the front panels 10, 12, 16 and 18, as well as the non-opaqued portions 13 and 17 are typically somewhat rectangular and, with the nose indentation 15*a*, 15 are designed to essentially lie against the user's cheeks below the eye socket. For effective use, this must essentially be the case or light input and/or the appearance of movement from one side or the other of the glasses may occur. It can be seen from FIG. 2 that the angular inclination of the glasses brings the lower edges 10*a* and 18*a* closely next to or in contact with the bases of the eye socket zones or cheek tops of the individual. This canting of the lenses to give space within the lenses or panels and the eyes below the brows causes the glasses to preferably require the rearwardly extended top edge 38, 21, and 24, whose inside edges essentially or preferably actually rest against or are slightly pressed against the eyebrow line of the user.

The distance between the pupils or centers of the pupils of the user fall in a statistical distribution around two and one-half inches. However, some peoples' eyes are closer together or further apart than others, which makes it, in some cases desirable to be able to vary the width of the non-opaqued portions 13 and 17.

It is almost necessary to have a resilient, deformable nose piece 15*a* to prevent the eyes from being able to see motion across the bridge of the nose.

The general opaquing may be produced by internal or external painting or taping or utilizing opaque material, per se, where called for. On the other hand, all opaquing may be produced by taping or painting over or under entirely transparent material. In such case, the "vertical" side lines of transparent panels 13 and 17 may be moved rightward or leftward, respectively (either boundary in either direction), to widen or narrow or transform and change the transparent panel. Their angles may be somewhat slanted. Thus, by adding additional tape in the left panel of FIG. 3 on the left edge, while removing tape from the right edge of the transparent area 13 will move the transparent area towards the nose guard. Removing tape from both edges widens the area of transparency. The right and left hand edges (or vertical edges 32 and 35) of areas 13 and 17 (one or both) may be moved right or left, respectively, to correspond with the left and right hand least ends 33 and 34 of the nose piece 15*a* without interfering with the sight picture. Wherever 31 and 32 and/or 35 and 36 may be, the center of vision panels 13 and 17 should be, as closely as possible, centered over the user's eye pupils.

Thus there is provided a pair of elongate front panels 10 and 12 and 16 and 18, joined centrally at 14, vertically overlying both eyes of any individual. Said front panels are typically somewhat rectangular, so as to substantially abut, each with its lower edge, the user's cheeks under the user's eyes. The side edges on the front panels are opaqued. Elongate, substantially normally vertical side panels 26 and 27, pivotally mounted at their front ends, each to a side edge of one front panel, are pivotally collapsible inwardly, one over the other, upon the rear side of the front panel and moveable outwardly from substantially parallel to one another (as shown) for use when mounted on the user's head.

The front panel end edges and side panel connections thereto are opaqued. User ear engagements are typically provided on the side panel free ends in normal glasses securing manner. The outer portions of the front panels are opaqued from their outward edges, inwardly, at least a limited distance.

A nose receiving indentation 15 in the lower center edge of said front panel 14 is provided, preferably with a resilient or spongy mount 15a thereon for comfort and light occlusion.

A portion of each said front panel above and adjacent to the nose indentation 15 is opaqued to the height of the top panel and forms, together with the side edge and panel opaquing on each side, a substantially uniform width limited viewing panel, 13 or 17, clear of opaquing in a limited portion thereof on each side of the nose indentation (in front of each eye).

The width of the center panel opaquing may be no greater than the width of the nose receiving indentation or the nose receiving pad 15a. The front panels, instead of actual clear plastic or glass may have viewing slots actually cut or molded therein a substantial proportion of the height of the panel in the non-opaque portions thereof. At least some of the opaquing may be obtained by addition of opaque adhesive tape to transparent structure on portions of the panels and end portions of the device in question. The top edge 21 of the front panels 10, 14 and 18 runs rearwardly from the top edges thereof in a normally substantial, horizontal orientation and use and at least portions thereof are preferably opaqued.

Referring to FIG. 3, sets of dotted lines have been applied thereto to show how the viewing ports, windows or slits in the glasses may be moved left or right, enlarged, slanted, etc. These lines will first be numbered, beginning at the left. Left of port 13 is line 31 with line 32 being to the right thereof. Moving right from 32 at 33 is the typical, at least minimum, opaquing (33, 34) of the center of the device. Line 34 is opposite to line 33. Around port 17, there are lines 35 and 36. Whether the opaque material is painted on the surface, inside or out or both, inherent in the material itself or caused by adhesive taping, the glasses structure, the relative positions of lines 31–36 inclusive may be initially set up in a manner differing from the showing of FIG. 1. or changed therefrom. When the opaquing is inherent in the material, the ports or windows 13 and 17 cannot be changed from the initial casting, as it were. If painting has produced the place, pattern and configuration of the windows 13 and 17 (or opaqued portions 10, 12, 14, 18, etc.) adding extra paint or tape for whatever effect desired is relatively easy. The paint may not be removable without scratching the lenses, on the other hand. When taping is employed, it is easy to replace or supplement the original taping with later, differently positioned tape strips. Applicant has discovered that some people may employ window ports with width from line 31 to line 33 for sight 13 and line 34 to line 36 for sight 17. It is thus seen that almost all variations between these limits may be employed.

On the other hand, using the 2.5 inches average eye pupil center separation, a modification of the invention as seen in the Figures without the dotted line optional variations may be employed. Typically, the desire is to maximize or optimize the width of openings, slots, windows, etc., 13 and 17, while effectively clearing the vision of the bowler from interference or being effected by motion in the two adjacent lanes or the four adjacent lanes, two on each side.

One starts with the assumption that a given eye has to be blocked centrally (over the nose piece) from sight to the second or first adjacent lane. Generally speaking, this can be done by blacking or opaquing off the nose piece width from its base straight upwardly. This coverage takes care of the cross nose looking from either eye. Then there is the outward viewing of each eye. This is taken care of by opaquing from the side edges 27, 11, 11a, 26, 20, and 19 (by opaquing inwardly toward the nose opaquing already in place). Quite a considerable panel of transparency may be provided as from 31 to 33 and 36 to 34, looking at FIG. 3. On the other hand, quite a limited panel of visibility centered on the eye pupil centers (approximately 2 and ½ inches apart) may be provided as in the construction seen in the drawings in full lines where the opaquing is essentially overdone to provide an absolutely controlled pair of panels of vision 13 and 17, which will accomplish the results of the invention.

From the foregoing, it will been seen that this invention is one well adapted to attain all of the ends and objects hereinabove set forth together with other advantages which are obvious and which are inherent to the apparatus.

As many possible embodiments may be made of the invention without departing from the scope thereof, it is to be understood that all matter herein set forth or shown in the accompanying drawings is to be interpreted as illustrative and not in a limiting sense.

I claim:

1. Eyeglasses for aiding bowling play by limiting peripheral vision comprising:

a pair of elongate front panels joined centrally normally substantially vertically overlying both eyes of any individual, said front panels typically somewhat rectangular, so as to substantially abut, with its lower edge, the user's cheeks under the user's eyes, normally vertical side edges on said front panels, said vertical side edges opaqued, elongate, substantially normally vertical side panels pivotally mounted at their front ends, each to a side edge of said front panel, said side panels pivotally collapsible, one over the other, upon the rear side of the front panels and moveable outwardly therefrom substantially parallel to one another for use;

the front panel end edges and side panel pivotal connections thereto substantially opaqued;

user ear engagements on the free ends of said side panels;

the outer portions of said front panel opaqued from outwardly inwardly at least a limited distance thereof forming a non-opaque portion;

a nose receiving indentation formed in the lower joined center edge of said front panel;

the portions of each said front panel above and adjacent to said indentation opaqued, formed together with the side edge and panel opaquing on each side, a substantially uniform width limited viewing panel clear of opaquing.

2. The eyeglasses as in claim 1 where in the width of the center panel opaquing is no greater than the width of the nose receiving indentation.

3. The eyeglasses as in claim 1 wherein the front panel has viewing slots cut therein a substantial proportion of the height of the panel in the non-opaque portions thereof.

4. The eyeglasses as in claim 1 wherein at least some of the opaquing is obtained by addition of adhesive tape, itself opaque, to portions of the panels and end portions of said vertical side panels.

5. The eyeglasses as in claim 1 wherein the top edge of the front panel runs rearwardly in a substantial, horizontal orientation and at least portions thereof are opaqued.

6. The eyeglasses of claim 1 wherein the front panels are arcuate in top plan view.

* * * * *